(12) United States Patent
Chung et al.

(10) Patent No.: US 12,264,211 B2
(45) Date of Patent: Apr. 1, 2025

(54) METHOD FOR PREPARING SUPER ABSORBENT POLYMER

(71) Applicant: LG Chem, Ltd., Seoul (KR)

(72) Inventors: Ui Seok Chung, Daejeon (KR); Kyu Pal Kim, Daejeon (KR); Gyunhyeok Ahn, Daejeon (KR); Gicheul Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1022 days.

(21) Appl. No.: 17/285,685

(22) PCT Filed: Aug. 11, 2020

(86) PCT No.: PCT/KR2020/010614
§ 371 (c)(1),
(2) Date: Apr. 15, 2021

(87) PCT Pub. No.: WO2021/054610
PCT Pub. Date: Mar. 25, 2021

(65) Prior Publication Data
US 2021/0317237 A1  Oct. 14, 2021

(30) Foreign Application Priority Data

Sep. 18, 2019 (KR) .................. 10-2019-0114791
Aug. 7, 2020 (KR) .................. 10-2020-0099393

(51) Int. Cl.
| | | |
|---|---|---|
| *C08F 2/22* | (2006.01) | |
| *A61L 15/60* | (2006.01) | |
| *B01J 20/26* | (2006.01) | |
| *B01J 20/28* | (2006.01) | |
| *C08F 2/44* | (2006.01) | |
| *C08F 6/14* | (2006.01) | |
| *C08F 220/06* | (2006.01) | |
| *C08F 283/06* | (2006.01) | |
| *C08J 3/075* | (2006.01) | |
| *C08J 3/12* | (2006.01) | |
| *C08J 3/24* | (2006.01) | |
| *C08K 3/011* | (2018.01) | |
| *C08K 3/30* | (2006.01) | |
| *C08K 5/06* | (2006.01) | |
| *C08K 5/09* | (2006.01) | |
| *C08K 5/5317* | (2006.01) | |

(52) U.S. Cl.
CPC .............. *C08F 2/22* (2013.01); *A61L 15/60* (2013.01); *B01J 20/261* (2013.01); *B01J 20/267* (2013.01); *B01J 20/28047* (2013.01); *C08F 2/44* (2013.01); *C08F 6/14* (2013.01); *C08F 220/06* (2013.01); *C08F 283/065* (2013.01); *C08J 3/075* (2013.01); *C08J 3/12* (2013.01); *C08J 3/245* (2013.01); *C08K 3/011* (2018.01); *C08K 3/30* (2013.01); *C08K 5/06* (2013.01); *C08K 5/09* (2013.01); *C08K 5/5317* (2013.01); *B01J 2220/68* (2013.01); *C08F 2810/20* (2013.01); *C08J 2205/022* (2013.01); *C08J 2333/02* (2013.01); *C08K 2003/3045* (2013.01)

(58) Field of Classification Search
CPC .. C08F 2/22; C08K 3/011; C08K 3/30; C08K 5/06; C08K 5/09; C08K 5/5317; C08K 2003/3045; A61L 15/60; B01J 20/261; B01J 20/267; B01J 20/28047; B01J 2220/68; C08J 3/075; C08J 3/12; C08J 3/245; C08J 2205/022; C08J 2333/02
USPC ............................................. 502/402
See application file for complete search history.

(56) References Cited

U.S. PATENT DOCUMENTS

| | | |
|---|---|---|
| 5,633,316 A | 5/1997 | Gartner et al. |
| 6,414,214 B1 | 7/2002 | Engelhardt et al. |
| 2004/0214946 A1 | 10/2004 | Smith et al. |
| 2010/0119312 A1 | 5/2010 | Nagashima et al. |
| 2010/0130950 A1 | 5/2010 | Harren et al. |
| 2010/0303869 A1 | 12/2010 | Azad et al. |
| 2012/0058267 A1 | 3/2012 | Stueven et al. |
| 2013/0296548 A1 | 11/2013 | Godin et al. |
| 2014/0194574 A1 | 7/2014 | Handa et al. |
| 2014/0332213 A1 | 11/2014 | Zhou et al. |
| 2015/0011388 A1 | 1/2015 | Matsumoto et al. |
| 2016/0024332 A1 | 1/2016 | Loick et al. |
| 2016/0207026 A1 | 7/2016 | Lee et al. |
| 2017/0014801 A1 | 1/2017 | Ikeuchi et al. |
| 2017/0166707 A1 | 6/2017 | Jang et al. |
| 2018/0265653 A1 | 9/2018 | Lee et al. |
| 2019/0194367 A1 | 6/2019 | Lee et al. |
| 2020/0047157 A1 | 2/2020 | Yang et al. |

(Continued)

FOREIGN PATENT DOCUMENTS

| | | |
|---|---|---|
| CN | 101310777 A | 11/2008 |
| CN | 105492465 A | 4/2016 |

(Continued)

OTHER PUBLICATIONS

Extended European Search Report including Written Opinion for Application No. 20864302.3 dated Oct. 11, 2021, pp. 1-5.

(Continued)

*Primary Examiner* — Edward M Johnson
(74) *Attorney, Agent, or Firm* — Lerner David LLP

(57) ABSTRACT

A method for preparing a super absorbent polymer is directed to appropriate control of the water content of the super absorbent polymer by hydration to suppress crushing during transfer. The method also provides suppression of deterioration of physical properties of the super absorbent polymer such as production of giant particles and nonuniformity of water content during a hydration step.

10 Claims, No Drawings

(56) References Cited

U.S. PATENT DOCUMENTS

| | | |
|---|---|---|
| 2020/0317872 A1 | 10/2020 | Wada et al. |
| 2021/0069674 A1 | 3/2021 | Jung et al. |

FOREIGN PATENT DOCUMENTS

| | | | |
|---|---|---|---|
| CN | 106164099 | A | 11/2016 |
| CN | 106795253 | A | 5/2017 |
| CN | 106893119 | A | 6/2017 |
| EP | 0505163 | A1 | 9/1992 |
| EP | 1462473 | A1 | 9/2004 |
| EP | 1622655 | A1 | 2/2006 |
| EP | 1187640 | B1 | 9/2006 |
| EP | 2135669 | A1 | 12/2009 |
| EP | 2752430 | A1 | 7/2014 |
| EP | 3708606 | A1 | 9/2020 |
| EP | 3722351 | A1 | 10/2020 |
| EP | 4089139 | A1 | 11/2022 |
| JP | H08120013 | A | 5/1996 |
| JP | H09124879 | A | 5/1997 |
| JP | 2007077393 | A | 3/2007 |
| JP | 2009051952 | A | 3/2009 |
| JP | 2010528128 | A | 8/2010 |
| JP | 2010241975 | A | 10/2010 |
| JP | 2010540004 | A | 12/2010 |
| JP | 2011092930 | A | 5/2011 |
| JP | 2012527502 | A | 11/2012 |
| JP | 5175352 | B2 | 4/2013 |
| JP | 2014237133 | A | 12/2014 |
| JP | 5989650 | B2 | 9/2016 |
| JP | 2017511416 | A | 4/2017 |
| JP | 2018203997 | A | 12/2018 |
| KR | 100333972 | B1 | 4/2002 |
| KR | 20060023116 | A | 3/2006 |
| KR | 20100019416 | A | 2/2010 |
| KR | 20150091363 | A | 8/2015 |
| KR | 20150141425 | A | 12/2015 |
| KR | 20160012961 | A | 2/2016 |
| KR | 101720423 | B1 | 3/2017 |
| KR | 20190012811 | A | 2/2019 |
| KR | 20190069103 | A | 6/2019 |
| KR | 20190069311 | A | 6/2019 |
| KR | 20190088830 | A | 7/2019 |
| WO | 0071176 | A1 | 11/2000 |
| WO | 2015129917 | A1 | 9/2015 |
| WO | 2019117541 | A1 | 6/2019 |
| WO | 2019143020 | A1 | 7/2019 |

OTHER PUBLICATIONS

International Search Report for Application No. PCT/KR2020/010614, mailed Nov. 30, 2020, 3 pages.

Odian, G, Principles of Polymerization, Second Edition, Copyright 1981 by John Wiley & Sons, Inc, p. 203.

Schwalm, R., UV Coatings; Basics, Recent Developments and New Applications, Dec. 21, 2006, p. 115, Elsevier Science.

International Search Report including Written Opinion for PCT/KR2020/010612 mailed Nov. 30, 2020; 9 pages.

Third Party Observation for Application No. PCT/KR2020/010612 submitted Jan. 17, 2022, pp. 1-9.

Third Party Observation for Application No. PCT/KR2020/010614 submitted Jan. 17, 2022, pp. 1-10.

Yamden Co., Ltd. "Texture measuring Instrument Creep Meter" Ipros Manufacturing, Feb. 2015, pp. 1-2. https://www.ipros.jp/product/detail/252170001.

METHOD FOR PREPARING SUPER ABSORBENT POLYMER

CROSS-REFERENCE TO RELATED APPLICATION(S)

The present application is a national phase entry under 35 U.S.C. § 371 of International Application No. PCT/KR2020/010614, filed on Aug. 11, 2020, which claims priority to Korean Patent Application No. 10-2019-0114791, filed on Sep. 18, 2019, and Korean Patent Application No. 10-2020-0099393, filed on Aug. 7, 2020, the disclosures of which are incorporated herein by reference in their entirety.

TECHNICAL FIELD

The present disclosure relates to a method for preparing a super absorbent polymer that can appropriately control a water content of the super absorbent polymer by hydration or the like to suppress crushing or the like during transfer, and also can suppress deterioration of physical properties, such as production of giant particles and nonuniformity of water content during hydration step.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For the application to such sanitary materials, super absorbent polymers typically have a form in which fine powders are compacted, and as these fine powders have a uniform particle size and a large surface area in sanitary materials, they need to exhibit the property of quickly absorbing a large amount of water.

On the other hand, in the process of preparing the super absorbent polymer, the super absorbent polymer is frequently transferred for the progress of subsequent process, packaging or application to sanitary materials, and the like. However, as the super absorbent polymer has a form in which fine powders are compacted, there are many cases where the super absorbent polymer powders physically collide and crush during the process of transferring the polymer. Consequently, there is a problem that various physical properties such as the overall absorbency of the super absorbent polymer are deteriorated.

To solve these problems, after finally preparing the super absorbent polymer, a hydration step of controlling the water content by adding a small amount of water while cooling the super absorbent polymer has been performed from the past. When the water content of the super absorbent polymer is partially increased by such hydration step, the overall crushing rate and degradation of physical properties may be greatly reduced during the transfer of the super absorbent polymer powder.

However, in the process of performing the hydration step, if sufficient and uniform mixing of the super absorbent polymer powders and water is not achieved, the polymer powders are compacted together, for example, a large amount of giant particles having a particle size larger than 850 μm (particles that cannot pass through the standard sieve #20) are often produced. The production of large amounts of such giant particles can lead to deterioration of the overall physical properties of the super absorbent polymer. Finally, it is necessary to add or remove the giant particles by a classification step or the like, which caused a deterioration in the overall productivity of the super absorbent polymer.

Due to the above-mentioned problems, there is a continuous demand for the development of a technology for preparing a super absorbent polymer that can appropriately control a water content of the super absorbent polymer by hydration or the like to suppress crushing or the like during transfer, and also can reduce problems such as production of giant particles during the hydration step.

DETAILED DESCRIPTION OF THE INVENTION

Technical Problem

It is one object of the present disclosure to provide a method for preparing a super absorbent polymer that can appropriately control a water content of the super absorbent polymer by hydration or the like to suppress crushing or the like during transfer, and also can suppress deterioration of physical properties, such as production of giant particles and nonuniformity of water content during hydration step.

Technical Solution

Therefore, according to the present disclosure, there is provided a method for preparing a super absorbent polymer comprising the steps of:
  providing super absorbent polymer particles comprising a base polymer powder including a cross-linked polymer of a water-soluble ethylenically unsaturated monomer having an acidic group of which at least a part is neutralized, and a surface cross-linked layer in which the cross-linked polymer is further cross-linked and which is formed on the base polymer powder, and
  mixing the super absorbent polymer particles with water and an additive including a carboxylic acid of an aliphatic hydrocarbon having 10 to 30 carbon atoms to form a hydrated super absorbent polymer.

Advantageous Effects

According to the method for preparing a super absorbent polymer of the present disclosure, as a specific additive is used in the hydration step, the water content of the super absorbent polymer can be appropriately controlled in the hydration step or the like to suppress crushing during transfer or degradation of physical properties. Furthermore, by the use of the specific additive, it is possible to solve the problem that the physical properties of the super absorbent polymer are deteriorated due to phenomena such as production of giant particles or nonuniformity of water content during the hydration step.

As a result, according to the present disclosure, since a decrease in physical properties or a deterioration in productivity due to the production of giant particles during the hydration step is substantially not shown while being able to suppress crushing during transfer of the super absorbent polymer, a super absorbent polymer exhibiting excellent physical properties can be prepared and transferred with high productivity, and thus can be preferably applied to the production of various sanitary materials.

DETAILED DESCRIPTION OF THE EMBODIMENTS

Although various modification may be made to the invention and the invention may have various forms, its specific examples are illustrated and will be described in detail below. However, it should be understood that this is not intended to limit the invention to particular forms disclosed herein, and the invention encompasses all modifications, equivalents or alternatives thereof without departing the spirit and technical scope of the present disclosure.

Hereinafter, the method for preparing a super absorbent polymer according to specific embodiments of the present disclosure will be described in more detail.

The technical terms used herein are only for reference to specific embodiments and is not intended to limit the present disclosure Unless otherwise specified throughout this specification. The singular terms used herein include plural terms unless phrases clearly express opposite meanings.

As used herein, the "polymer" or "macromolecule" refers to the polymerized state of water-soluble ethylenically unsaturated monomers, and may encompass those of all water content ranges or particle size ranges. Among the polymers, those having water content (moisture content) of about 40 wt. % or more after polymerized and before dried may be designated as hydrogel polymer.

And, the "super absorbent polymer" means the polymer or base polymer itself according to the context, or it is used to include those made to be appropriate for productization through additional processes, for example, surface cross-linking, fine particle reassembly, drying, pulverization, classification, hydration, etc. of the polymer or the base polymer.

According to some embodiments of the present disclosure, there is provided a method for preparing a super absorbent polymer comprising the steps of:
providing super absorbent polymer particles comprising a base polymer powder including a cross-linked polymer of a water-soluble ethylenically unsaturated monomer having an acidic group of which at least a part is neutralized, and a surface cross-linked layer in which the cross-linked polymer is further cross-linked and which is formed on the base polymer powder, and
mixing the super absorbent polymer particles with water and an additive including a carboxylic acid of an aliphatic hydrocarbon having 10 to 30 carbon atoms to form a hydrated super absorbent polymer.

In the preparation method of some embodiments, after a super absorbent polymer is prepared by proceeding up to a surface crosslinking, while performing a hydration step of the super absorbent polymer, a small amount of an additive including an aliphatic hydrocarbon functional group having 10 or more carbon atoms and a carboxylic acid functional group in the molecular structure is added together. The above additive has a long-chain hydrocarbon hydrophobic functional group in its molecule and also has a carboxylic acid hydrophilic functional group at the terminal end.

It was confirmed that by adding these specific additives together in the hydration step, the aggregation phenomenon between polymer particles can be significantly reduced during the progress of the hydration step. This is considered to be because a hydrophobic functional group of the long-chain hydrocarbon may delay the contact and water absorption between the polymer particles and the water added in the hydration step. As a result, aggregation between super absorbent polymer particles, formation of giant particles, and deterioration of physical properties can be suppressed during the hydration step and the transfer step.

Moreover, since the specific additive contains the hydrophobic functional group together with the hydrophilic functional group of the carboxylic acid, it allows the super absorbent polymer particles to be evenly dispersed and distributed in the mixed water, thereby more effectively suppressing crushing and the like during transfer of the super absorbent polymer.

As a result, according to the preparation method of some embodiments, the water content of the super absorbent polymer can be appropriately controlled in the hydration step or the like to suppress crushing or degradation of physical properties during transfer of the super absorbent polymer, and also it is also possible to solve the problem that physical properties of the super absorbent polymer are deteriorated due to phenomena such as production of giant particles or nonuniformity of water content during hydration step.

On the other hand, when other additives different from the method of some embodiments, for example, a polycarboxylic acid copolymer conventionally known as an aggregation inhibitor, or polyethylene glycol, which is a typical hydrophilic polymer, are used in the hydration step, it was confirmed that aggregation in the hydration step is not properly suppressed, and a large amount of giant particles exceeding 850 µm are produced or the water content becomes non-uniform, thereby exhibiting a decrease in overall physical properties or a deterioration in productivity of the super absorbent polymer. This is predicted because a large number of hydrophilic functional groups exist in the polymer.

As such, according to the method of some embodiments, since a decrease in physical properties or a deterioration in productivity due to the production of giant particles during the hydration step is substantially not shown while being able to effectively suppress crushing during transfer of the super absorbent polymer, a super absorbent polymer exhibiting excellent physical properties can be prepared and transferred with high productivity, and thus can be preferably applied to the production of various sanitary materials.

Hereinafter, a method for preparing a super absorbent polymer according to some embodiments will be described in more detail for each step.

In the method of preparing a super absorbent polymer according to some embodiments, first, super absorbent polymer particles are prepared. These super absorbent polymer particles can be prepared through crosslinking polymerization, drying, pulverization, classification, surface crosslinking and the like in accordance with the preparation process and conditions of a general super absorbent polymer. Hereinafter, an example of preparing the super absorbent polymer particles will be described in detail.

First, a monomer composition is prepared by mixing respective components of a water-soluble ethylenically unsaturated monomer having an acidic group of which at least a part is neutralized, an internal crosslinking agent and a polymerization initiator.

The water-soluble ethylenically unsaturated monomer may be any monomer commonly used for the preparation of a super absorbent polymer. As a non-limiting example, the water-soluble ethylenically unsaturated monomer may be a compound represented by the following Chemical Formula 1:

$$R_1\text{—COOM}^1 \qquad \text{[Chemical Formula 1]}$$

in the Chemical Formula 1, $R_1$ is an alkyl group having 2 to 5 carbon atoms containing an unsaturated bond, and $M^1$ is a hydrogen atom, a monovalent or divalent metal, an ammonium group or an organic amine salt.

Suitably, the monomer may be one or more selected from the group consisting of acrylic acid, methacrylic acid, and monovalent metal salts, divalent metal salts, ammonium salts, and organic amine salts of these acids. When a (meth)acrylic acid and/or a salt thereof is used as the water-soluble ethylenically unsaturated monomer in this way, it is advantageous in that a super absorbent polymer having improved water absorptivity can be obtained. In addition, as the monomer, an anionic monomer such as maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, and a salt thereof; a non-ionic hydrophilic group-containing monomer such as (meth)acrylamide, N-substituted (meth) acrylate, 2-hydroxyethyl(meth)acrylate, 2-hydroxypropyl (meth)acrylate, methoxypolyethyleneglycol(meth)acrylate, or polyethyleneglycol(meth)acrylate; and an amino group-containing unsaturated monomer such as (N,N)-dimethyl-aminoethyl(meth)acrylate, or (N,N)-dimethylaminopropyl (meth)acrylamide, and a quaternary compound thereof may be used.

Here, the water-soluble ethylenically unsaturated monomers may have an acidic group, in which at least a part of the acidic group may be neutralized. Preferably, those in which the monomer is partially neutralized with an alkaline substance such as sodium hydroxide, potassium hydroxide, ammonium hydroxide or the like can be used.

In this case, a degree of neutralization of the monomer may be 40 to 95 mol %, or 40 to 80 mol %, or 45 to 75 mol %. The range of the degree of neutralization may vary depending on the final physical properties. However, an excessively high degree of neutralization causes the neutralized monomers to be precipitated, and thus polymerization may not readily occur, whereas an excessively low degree of neutralization not only greatly deteriorates the absorbency of the polymer, but also endows the polymer with hard-to-handle properties, like elastic rubber.

Meanwhile, the internal crosslinking agent is a term used to distinguish it from the surface crosslinking agent for further crosslinking the surface of the base polymer described later, and serves to perform crosslinking polymerization of the unsaturated bond of the above-mentioned water-soluble ethylenically unsaturated monomer. The crosslinking in the above step proceeds without distinction between the surface or the interior, but by the surface crosslinking step of the base polymer described later, the surface of the finally prepared super absorbent polymer is composed of a structure cross-linked by a surface crosslinking agent, and the interior is composed of a structure cross-linked by the internal crosslinking agent.

As the internal crosslinking agent, any compound can be used as long as it enables introduction of a crosslink bond upon polymerization of the water-soluble ethylenically unsaturated monomer. Non-limiting examples of the internal crosslinking agent may include multifunctional crosslinking agents, such as N,N'-methylenebisacrylamide, trimethylolpropane tri(meth)acrylate, (poly)ethylene glycol di(meth) acrylate, polyethylene glycol(meth)acrylate, (poly)propylene glycol di(meth)acrylate, polypropylene glycol(meth) acrylate, butanediol di(meth)acrylate, (poly)butylene glycol di(meth)acrylate, diethylene glycol di(meth)acrylate, hexanediol di(meth)acrylate, triethylene glycol di(meth) acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, alkylene glycol diglycidyl ether compound such as ethylene glycol diglycidyl ether, propylene glycol, glycerin, or ethylene carbonate, which may be used alone or in combination of two or more thereof, but are not limited thereto.

Such an internal crosslinking agent may be used in an amount of 0.01 to 5 parts by weight based on 100 parts by weight of the water-soluble ethylenically unsaturated monomer. For example, the internal crosslinking agent may be used in an amount of 0.01 parts by weight or more, 0.03 parts by weight or more, or 0.05 parts by weight or more, and 5 parts by weight or less or 3 parts by weight or less, based on 100 parts by weight of the water-soluble ethylenically unsaturated monomer. When the content of the internal crosslinking agent is excessively low, crosslinking does not occur sufficiently, which may make it difficult to implement strength at an appropriate level or higher, and when the content of the internal crosslinking agent is excessively high, the internal crosslinking density becomes high, which may make it difficult to implement the required absorption performance.

Further, the polymerization initiator can be properly selected depending on the polymerization method. In the case of a thermal polymerization, a thermal polymerization initiator is used, and in the case of a photo-polymerization, a photo-polymerization initiator is used. Further, in the case of a mixed polymerization method (a method using both heat and light) is used, both the thermal polymerization initiator and the photo-polymerization initiator can be used. However, even in the case of the photo-polymerization method, because a certain amount of heat is generated by the ultraviolet irradiation or the like and heat is generated to some degree according to the progress of the exothermic polymerization reaction, a thermal polymerization initiator may be additionally used.

The photo-polymerization initiator can be used without any limitation in its constitution as long as it is a compound capable of forming a radical by a light such as ultraviolet rays.

The photo-polymerization initiator, for example, may include at least one selected from the group consisting of a benzoin ether, a dialkyl acetophenone, a hydroxyl alkylketone, a phenyl glyoxylate, a benzyl dimethyl ketal, an acyl phosphine, and an α-aminoketone. Meanwhile, specific examples of the acyl phosphine may include diphenyl(2,4, 6-trimethylbenzoyl) phosphine oxide, phenyl bis(2,4,6-trimethylbenzoyl)phosphine oxide, ethyl(2,4,6-trimethylbenzoyl)phenylphosphinate, and the like. More various photo-polymerization initiators are well disclosed in "UV Coatings: Basics, Recent Developments and New Application" written by Reinhold Schwalm, (Elsevier, 2007), p 115, however the photo-polymerization initiator is not limited to the above-described examples.

The photo-polymerization initiator may be included in a concentration of about 0.0001 to about 2.0% by weight with respect to the monomer composition. When the concentration of the photo-polymerization initiator is excessively low, the polymerization rate may become slow, and when the concentration of the photo-polymerization initiator is excessively high, the molecular weight of the super absorbent polymer may become small and its physical properties may become uneven.

Further, as the thermal polymerization initiator, at least one selected from the group consisting of persulfate-based initiator, azo-based initiator, hydrogen peroxide and ascorbic acid can be used. Specifically, examples of the persulfate-based initiators include sodium persulfate ($Na_2S_2O_8$), potassium persulfate ($K_2S_2O_8$), ammonium persulfate (($NH_4)_2S_2O_8$) and the like, and examples of the azo-based initiator include 2,2-azobis(2-amidinopropane)dihydrochloride, 2,2-azobis-(N,N-dimethylene)isobutyramidine dihydrochloride, 2-(carbamoylazo)isobutylonitrile, 2,2-azobis [2-(2-imidazolin-2-yl)propane]dihydrochloride, 4,4-azobis-(4-cyanovaleric acid) and the like. More various thermal polymerization initiators are well disclosed in "Principle of Polymerization" written by Odian, (Wiley, 1981), p 203, however the thermal polymerization initiator is not limited to the above-described examples.

The thermal polymerization initiator can be included in the concentration of about 0.001 to about 2.0% by weight with respect to the monomer composition. When the concentration of the thermal polymerization initiator is excessively low, the additional thermal polymerization hardly occurs and thus effects due to the addition of the thermal polymerization initiator may be insignificant, and when the concentration of the thermal polymerization initiator is excessively high, the molecular weight of the super absorbent polymer becomes small and the physical properties may become uneven.

The above-mentioned monomer composition may further include additives such as a thickener, a plasticizer, a preservation stabilizer, an antioxidant, a surfactant, and the like, if necessary.

The above-mentioned water-soluble ethylenically unsaturated monomer, the internal crosslinking agent and the polymerization initiator may be mixed with a solvent. Therefore, the monomer composition prepared in the above step is in a form dissolved in the solvent, and the amount of the solid content in the monomer composition may be 20 to 60% by weight.

In this case, the solvent can be used without limitation in its constitution as long as it can dissolve the above-mentioned components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination with each other.

Meanwhile, the mixing of the above-mentioned components is not particularly limited, and may be performed through a method commonly used in the art, for example, stirring.

Next, the step of subjecting the monomer composition to a crosslinking polymerization to form a hydrogel polymer is performed.

The step is not particularly limited in terms of its configuration as long as the monomer composition can be subjected to a crosslinking polymerization by the thermal polymerization, photo-polymerization or mixed polymerization method to form a hydrogel polymer.

Specifically, in the case of the thermal polymerization, it can be performed in a reactor like a kneader equipped with agitating spindles. Further, the thermal polymerization may be performed at a temperature of about 80° C. or more and less than about 110° C. Means for achieving the polymerization temperature within the above-mentioned range is not particularly limited. Heating may be performed by providing a heating medium to the reactor or by directly providing a heat source. The type of the heating medium that can be used may be a heated fluid such as steam, hot air, hot oil, etc., but is not limited thereto. Further, the temperature of the heating medium provided may be properly selected in consideration of the means of the heating medium, the temperature raising speed, and the temperature raising target temperature. Meanwhile, a heating method using electricity or a heating method using gas may be used as the heat source provided directly, but the heat source is not limited to the above-described examples.

Meanwhile, in the case of the photo-polymerization, it can be performed in a reactor equipped with a movable conveyor belt, but the above-mentioned polymerization method is merely an example, and the present disclosure is not limited to the above-mentioned polymerization method.

As an example, when the thermal polymerization is performed by providing a heat medium to a reactor such as a kneader equipped with a stirring spindle or heating the reactor as described above, the hydrogel polymer that is discharged from the outlet of the reactor can be obtained. The hydrogel polymer thus obtained may have a size of several centimeters to several millimeters, according to the shape of the stirring spindle equipped in the reactor. Specifically, the size of the obtained hydrogel polymer may vary according to the concentration of the monomer composition injected thereto, the injection speed, or the like.

Further, as described above, when the photo-polymerization is performed in a reactor equipped with a movable conveyor belt, the obtained hydrogel polymer may be usually a sheet-like hydrogel polymer having a width of the belt. In this case, the thickness of the polymer sheet may vary depending on the concentration and the injection speed of the monomer composition to be injected thereto, but usually, it is preferable to supply the monomer composition so that a sheet-like polymer having a thickness of about 0.5 to about 10 cm can be obtained. When the monomer composition is supplied to such an extent that the thickness of the sheet-like polymer becomes too thin, it is undesirable because the production efficiency is low, and when the thickness of the sheet-like polymer is greater than 10 cm, the polymerization reaction cannot be evenly performed over the entire thickness because of the excessive thickness.

The polymerization time of the monomer composition is not particularly limited, and may be controlled from about 30 seconds to 60 minutes.

The hydrogel polymer obtained by the above-mentioned method may have a water content of about 30 to about 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content can be defined as a value calculated by measuring the weight loss due to evaporation of water in the polymer in the process of drying by raising the temperature of the polymer through infrared heating. At this time, the drying conditions are follows: the drying temperature is increased from room temperature to about 180° C. and then the temperature is maintained at 180° C., and the total drying time is set to 40 minutes, including 5 minutes for the temperature rising step.

Next, the step of drying, pulverizing and classifying the hydrogel polymer to form a base polymer in the form of a powder is performed.

Meanwhile, in the step of forming the base polymer, a coarsely pulverizing step may be included before drying the hydrogel polymer in order to increase the efficiency of the drying step.

A pulverizing machine used here is not limited in terms of its configuration, and specifically, it may include any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

Through the coarsely pulverizing step, the particle size of the hydrogel polymer can be controlled to about 0.1 to about 10 mm. Pulverizing the hydrogel polymer into a particle size of less than 0.1 mm is technically not easy due to its high water content, and aggregation phenomenon between the pulverized particles may occur. Meanwhile, if the polymer is pulverized into a particle size of greater than 10 mm, the effect of increasing the efficiency in the subsequent drying step may be insignificant.

The hydrogel polymer coarsely pulverized as above or the hydrogel polymer immediately after polymerization without the coarsely pulverizing step is subjected to a drying step. In this case, the drying temperature may be about 60° C. to about 250° C. When the drying temperature is less than about 70° C., it is likely that the drying time becomes too long, and when the drying temperature is higher than about 250° C., only the surface of the polymer is excessively dried, and thus it is likely that fine powder is generated during the subsequent pulverizing step, and the physical properties of the super absorbent polymer finally formed is deteriorated. Therefore, preferably, the drying may be performed at a temperature of about 100° C. to about 240° C., more preferably about 110° C. to about 220° C.

Further, the drying time may be about 20 minutes to about 12 hours, in consideration of the process efficiency and the like. As an example, it may be dried for about 10 minutes to about 100 minutes, or about 20 minutes to about 60 minutes.

In the drying step, the drying method may also be selected and used without being limited by its constitution if it is a method commonly used for drying the hydrogel polymer. Specifically, the drying step may be carried out by a method such as hot air supply, infrared irradiation, microwave irradiation or ultraviolet irradiation. After the drying step as above is carried out, the water content of the polymer may be about 0.1 to about 10% by weight.

Subsequently, the dried polymer obtained through the drying step is pulverized using a pulverizing device.

Specifically, the base polymer in the form of powder obtained through the pulverizing step may have a particle size of about 150 μm to about 850 μm. As a pulverizing device for pulverizing into such particle size, a pin mill, a hammer mill, a screw mill, a roll mill, a disc mill or a jog mill, etc. may be used, but the pulverizing device is not limited thereto.

And, in order to control the physical properties of the super absorbent polymer powder finally commercialized after the pulverization step, a separate step of classifying the polymer powder obtained after the pulverization depending on the particle size may be undergone. Preferably, a polymer having a particle size of about 150 to about 850 μm is classified and only the polymer powder having such a particle size is subjected to the surface crosslinking reaction and finally commercialized. More specifically, the classified base polymer powder may have a particle size of 150 to 850 μm, and may include 50% by weight or more of particles having a particle size of 300 to 600 μm.

On the other hand, after forming the base polymer through the above-mentioned classification step, a step of further crosslinking the surface of the base polymer in the presence of a surface crosslinking agent to form a surface cross-linked layer is performed.

The above step is a step of forming a surface cross-linked layer using a surface crosslinking agent in order to increase the surface crosslinking density of the base polymer, wherein the unsaturated bonds of the water-soluble ethylenically unsaturated monomer that remained on the surface without being cross-linked are cross-linked by the surface crosslinking agent, thereby forming a super absorbent polymer having a high surface crosslinking density. The surface crosslinking density, that is, the external crosslinking density, is increased by this surface crosslinking step, while the internal crosslinking density does not change, so that the super absorbent polymer in which the surface cross-linked layer is formed has a structure in which the crosslink density on the outside is higher than that on the inside.

In the method of some embodiments, a surface crosslinking agent composition including a surface crosslinking agent, an alcohol-based solvent, and water may be used in the step of forming the surface cross-linked layer.

Meanwhile, as the surface crosslinking agent contained in the surface crosslinking agent composition, any surface crosslinking agent conventionally used for the preparation of a super absorbent polymer can be used without particular limitation. For example, the surface crosslinking agent may include at least one polyol selected from the group consisting ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; at least one carbonate-based compound selected from the group consisting of ethylene carbonate and propylene carbonate; an epoxy compound such as ethylene glycol diglycidyl ether; oxazoline compounds such as oxazolidinone; polyamine compounds; oxazoline compounds; mono-, di- or polyoxazolidinone compounds; or cyclic urea compounds; and the like.

Preferably, the same internal crosslinking agent as described above may be used, and for example, an alkylene glycol diglycidyl ether-based compound such as ethylene glycol diglycidyl ether may be used.

The surface crosslinking agent can be used in an amount of 0.001 to 2 parts by weight based on 100 parts by weight of the base polymer. For example, the surface crosslinking agent may be used in an amount of 0.005 parts by weight or more, 0.01 parts by weight or more, or 0.02 parts by weight or more, and 0.5 parts by weight or less or 0.3 parts by weight or less based on 100 parts by weight of the base polymer. By adjusting the content range of the surface crosslinking agent within the above-mentioned range, it is possible to prepare a super absorbent polymer exhibiting various physical properties such as excellent absorption performance and liquid permeability.

Further, the method of mixing the surface crosslinking agent composition with the base polymer is not particularly limited in terms of its configuration. For example, a method of placing the surface crosslinking solution and the base polymer powder into a reaction tank and mixing them, a method of spraying a surface crosslinking solution onto the base polymer powder, a method in which the base polymer powder and the surface crosslinking solution are continuously supplied in a continuously operating mixer and mixed, or the like can be used.

The surface crosslinking step may be performed at a temperature of about 80° C. to about 250° C. More specifically, the surface crosslinking step may be performed at a temperature of about 100° C. to about 220° C., or about 120° C. to about 200° C. for about 20 minutes to about 2 hours, or about 40 minutes to about 80 minutes. When the conditions of the above-mentioned surface crosslinking step are satisfied, the surface of the base polymer is sufficiently cross-linked, and thus, the absorbency under pressure or liquid permeability may be increased.

A means for raising the temperature for surface crosslinking reaction is not particularly limited. Heating may be performed by providing a heating medium or by directly providing a heat source. The type of the heating medium applicable herein may be a hot fluid such as steam, hot air, hot oil, or the like, but is not limited thereto. Further, the temperature of the heating medium provided may be properly selected, considering the means of the heating medium, the temperature-raising rate, and the temperature-raising target temperature. Meanwhile, as the heat source provided directly, an electric heater or a gas heater may be used, but is not limited to the above-described examples.

On the other hand, by proceeding up to the surface crosslinking step through the steps exemplified above, super absorbent polymer particles may be produced and provided. Such super absorbent polymer particles can, for example, have a form including a base polymer powder containing a cross-linked polymer in which a water-soluble ethylene-based unsaturated monomer having at least a partially neutralized acidic group is polymerized via an internal cross-linking agent, and a surface cross-linked layer in which the cross-linked polymer is further cross-linked and which is formed on the base polymer powder.

Further, the super absorbent polymer particles may be in a form in which fine powders having a particle size of 150 to 850 μm are compacted so that a large amount of water can be rapidly absorbed over a large surface area in the sanitary material.

By the way, such super absorbent polymer particles may be crushed by physical collision or the like in the process of being transferred to a subsequent packaging process, a subsequent preparation process of sanitary material, or the like. Thus, in order to suppress this, a hydration step of mixing the super absorbent polymer particles with a predetermined additive and water to form a hydrated super absorbent polymer is performed.

In such a hydration step, as already described above, a carboxylic acid of an aliphatic hydrocarbon having 10 to 30 carbon atoms is used as an additive. As the additive has both a hydrophobic functional group of a long-chain hydrocarbon and a hydrophilic functional group of carboxylic acid in the molecule, the crushing and aggregation phenomenon of the super absorbent polymer during the hydration step and the transport can be effectively suppressed.

In a more specific example, the additive may be a compound in which a carboxylic acid is bonded to the end of an aliphatic saturated hydrocarbon such as a linear alkyl group having 12 to 20 carbon atoms. In a more specific example, it may be one or more carboxylic acid compounds selected from the group consisting of stearic acid, lauric acid, and arachidic acid.

By using such a compound as an additive during the hydration step, it is possible to more effectively suppress the formation of giant particles due to crushing and aggregation during the hydration step and the transfer of the super absorbent polymer, and the deterioration of the physical properties of the super absorbent polymer resulting therefrom.

In addition, the above-mentioned additive may be mixed in an amount of 5 to 20,000 ppmw based on the weight of the super absorbent polymer particles so as not to inhibit the uniform increase in water content due to the hydration step, even while effectively suppressing the formation of giant particles due to aggregation of the super absorbent polymer particles during the hydration step. In a more specific example, the additive may be mixed in an amount of 5 to 1000 ppmw, 10 to 500 ppmw, or 50 to 300 ppmw based on the weight of the super absorbent polymer particles.

As the additive is used within such content range, the water content of the super absorbent polymer can be uniformly controlled as a whole within a desired range by the hydration step, a subsequent drying and the like, while more effectively suppressing the aggregation between super absorbent polymer particles and the formation of giant particles during the hydration step.

On the other hand, in order for water to be uniformly mixed with the super absorbent polymer particles in the hydration step to thereby uniformly control the water content of the final super absorbent polymer as a whole, the water is preferably mixed in an amount of 1 to 10 parts by weight, 3 to 8 parts by weight, or 4 to 6 parts by weight based on 100 parts by weight of the super absorbent polymer particles.

The hydration step of mixing the super absorbent polymer particles and water and the above-mentioned additive may be performed while cooling the surface cross-linked super absorbent polymer particles under a temperature of, for example, 40 to 80° C. or 45 to 75° C. Thereby, deterioration of the physical properties of the super absorbent polymer can be suppressed while simplifying the overall process.

After the hydration step is performed by the above-mentioned method to form the hydrated superabsorbent polymer, a step of drying and classifying the hydrated super absorbent polymer may be further performed. While drying the hydrated superabsorbent polymer in which water and additives are uniformly mixed in the hydration step, a desired water content, for example, a water content of 1 to 2.5% by weight may be achieved. Such water content range is increased as compared with the water content of the super absorbent polymer particles immediately after surface cross-linking of about 0.5% by weight or less, or 0.3% by weight or less. Due to the constant increase in the water content, physical crushing can be effectively suppressed during transport of the super absorbent polymer.

Such drying step can be performed under a drying apparatus and conditions equivalent to those performed in the preparation process of super absorbent polymer particles, and in consideration of the target water content, a person skilled in the art can proceed for an appropriate drying time.

Meanwhile, after achieving the target moisture content through the drying, the super absorbent polymer may be further classified. In the process of additional classification, giant particles generated in the hydration step, for example, particles having a particle size of more than 850 μm and particles having a particle size of less than 150 μm may be removed, and the super absorbent polymer may be prepared to have a particle size of 150 to 850 μm.

However, in the method of some embodiments, as a specific additive is used in the process of hydration, the production of giant particles by the hydration may be greatly reduced. Therefore, the particles having a particle size of more than 850 μm removed in the process of classification may be less than 5% by weight, or less than 3% by weight, or 0.1 to 3% by weight based on the total weight of the dried super absorbent polymer.

In contrast, when an additive is not used during the hydration step or other additives different from the method of some embodiments are used, a lot of giant particles are generated during the hydration step, so that the particles having a particle size of more than 850 μm removed in the process of classification may be about 20% by weight or more based on the total weight of the dried super absorbent polymer.

Meanwhile, the super absorbent polymer finally prepared by the method according to some embodiments via the process of drying and classification described above has a centrifuge retention capacity (CRC) for a physiological saline solution (0.9 wt. % aqueous sodium chloride solution) for 30 minutes, of 30 to 45 g/g when measured for the polymer having a particle size of 150 to 850 μm, thereby maintaining excellent absorption performance. The centrifuge retention capacity may be measured in accordance with EDANA (European Disposables and Nonwovens Association) recommended test method No. WSP 241.3 and may be calculated according to the Equation A described in Test Example described later.

The dried and classified super absorbent polymer described above may be further transferred for application in subsequent packaging, sanitary material preparation processes, and the like. Such super absorbent polymer does not substantially cause crushing or deterioration of physical properties even during the transfer process by appropriately controlling the water content. Furthermore, since the formation of giant particles is also minimized in the hydration step, it can be produced so as to have excellent physical properties and productivity as a whole.

Hereinafter, preferred examples are presented to aid in understanding the invention. However, the following examples are for illustrative purposes only, and the invention is not limited thereto.

EXAMPLE

Example 1: Preparation of Super Absorbent Polymer 100 g of acrylic acid, 123.5 g of 32% caustic soda, 0.2 g of sodium persulfate as a thermal polymerization initiator, 0.008 g of diphenyl (2,4,6-trimethylbenzoyl)-phosphine oxide as a photo-initiator, 2.25 g of polyethylene glycol diacrylate as an internal crosslinking agent and 59.0 g of water were mixed to prepare a monomer composition having a total solid content concentration of 45 wt. %. The monomer composition was supplied at a rate of 500 mL/min to 2000 mL/min on a rotating belt having a width of 10 cm and a length of 2 m and rotating at a speed of 50 cm/min. The supplied monomer composition was irradiated with ultraviolet rays at an intensity of 10 mW/cm$^2$ and subjected to a crosslinking polymerization for 60 seconds.

After the crosslinking polymerization reaction, the hydrogel polymer was coarsely pulverized with a meat chopper, and was dried at 190° C. for 40 minutes using an air-flow oven.

In 100 g of the base polymer thus prepared, a surface crosslinking agent composition, which is a mixed solution of 3 g of ultrapure water, 3.5 g of methanol, 0.25 g of 1,3-propanediol, and 0.16 g of oxalic acid, was charged, and mixed for 2 minutes. The mixture was heat-treated at 185° C. for 50 minutes and subjected to a surface crosslinking, and then classified to take particles having a particle size of 150 to 850 μm, thereby preparing super absorbent polymer particles.

Then, while rotating 200 g of the super absorbent polymer particles in a crucible at 60° C., a mixed solution of 10 g of ultrapure water and 0.0250 g of lauric acid was charged and mixed for 2 minutes. The result was further dried for 25 minutes and then classified to obtain a final product.

Example 2: Preparation of Super Absorbent Polymer

A final product of a super absorbent polymer was obtained in the same manner as in Example 1, except that 0.0250 g of stearic acid was used instead of 0.0250 g of lauric acid.

Example 3: Preparation of Super Absorbent Polymer

A final product of a super absorbent polymer was obtained in the same manner as in Example 1, except that 0.0250 g of arachidic acid was used instead of 0.0250 g of lauric acid.

Comparative Example 1: Preparation of Super Absorbent Polymer

First, the super absorbent polymer particles were prepared in the same manner as in Example 1. However, superabsorbent polymer particles themselves were used as the final produce of the super absorbent polymer of Comparative Example 1, without proceeding the step of charging and mixing the mixed solution of ultrapure water and lauric acid, which was further performed in Example 1, and the subsequent steps of additional drying and classification.

Comparative Example 2: Preparation of Super Absorbent Polymer

First, the super absorbent polymer particles were prepared in the same manner as in Example 1.

Then, 10 g of ultrapure water not mixed with lauric acid was charged and mixed for 2 minutes, while rotating 200 g of the super absorbent polymer particles in a crucible at 60° C. The result was further dried for 25 minutes and then classified to obtain a final product.

Comparative Example 3: Preparation of Super Absorbent Polymer

A final product of a super absorbent polymer was obtained in the same manner as in Example 1, except that 0.0250 g of a polycarboxylic acid copolymer disclosed in Preparation Example 1 of Korean Unexamined Patent Publication No. 2015-0143167 was used instead of 0.0250 g of lauric acid.

Comparative Example 4: Preparation of Super Absorbent Polymer

A final product of a super absorbent polymer was obtained in the same manner as in Example 1, except for 0.25 g of polyethylene glycol with Mw 600 was used instead of 0.0250 g of lauric acid.

Test Example various physical properties of the super absorbent polymer prepared in Examples and Comparative Examples were measured by the following method, and the results are shown in Table 1 below.

(1) Centrifuge Retention Capacity (CRC)

First, the super absorbent polymer having a particle size of 150 to 850 μm (between the standard sieve size of #20 to 100) was taken, and the centrifuge retention capacity (CRC) by water absorption capacity under a non-loading condition was measured in accordance with EDANA (European Disposables and Nonwovens Association) recommended test method No. WSP 241.3.

Specifically, the super absorbent polymer (or base polymer powder; hereinafter the same) $W_0$ (g, about 0.2 g) was uniformly put in a nonwoven fabric-made bag and sealed, and the bag was immersed in a physiological saline solution (0.9 wt. % sodium chloride aqueous solution) at room temperature. After 30 minutes, water was removed from the bag by centrifugation at 250 G for 3 minutes, and the weight $W_2$ (g) of the bag was then measured. In addition, the same procedure was carried out without using the super absorbent polymer, and then the resultant weight $W_1$ (g) was measured. Using the respective weights thus obtained, CRC (g/g) was calculated according to the following Equation A to confirm the centrifuge retention capacity:

$$\text{CRC (g/g)} = \{[W_2 (g) - W_1 (g) - W_0 (g)] / W_0 (g)\} \qquad \text{[Equation A]}$$

(2) Particle Size Distribution

In order to measure the particle size distribution, a super absorbent polymer was classified using a standard sieve of ASTM standards. More specifically, standard sieves each having mesh sizes of 850 μm, 600 μm, 300 μm, and 150 μm were sequentially stacked, and then 100 g of a super absorbent polymer was put on the top, and set in a sieve shaker (AS200). Classification was performed for 10 minutes at an amplitude of 1.0 mm/g. The super absorbent polymer remaining between standard sieves was taken out, weighed, and calculated as a percentage, thereby calculating the particle size distribution of the super absorbent polymer.

(3) Water Content

The water content was determined as a value calculated by measuring the weight loss due to evaporation of water in the super absorbent polymer in the process of drying the super absorbent polymer while heating it with infrared rays. At this time, the drying conditions were set such that the drying temperature was increased from room temperature to about 140° C., and then the temperature was maintained at 140° C., and the total drying time was 10 minutes. The water content was calculated from the measurement result of the weight loss.

TABLE 1

| Physical properties | | Comparative Example 1 | Comparative Example 2 | Comparative Example 3 | Comparative Example 4 | Example 1 | Example 2 | Example 3 |
|---|---|---|---|---|---|---|---|---|
| | CRC (#20~100; g/g) | 33.4 | 31.8 | 32.0 | 31.5 | 31.9 | 32.0 | 32.8 |
| | Water content (#20~100; wt. %) | 0.3 | 2.2 | 1.98 | 1.89 | 1.71 | 1.60 | 1.79 |
| Particle size distribution | Less than #20 (more than 850 μm) | 0.4 | 39.3 | 21.2 | 20.0 | 0.8 | 0.7 | 0.4 |
| | #20~30 (600~850 μm) | 17.2 | 30.0 | 31.2 | 30.6 | 20.9 | 21.3 | 19.8 |
| | #30~50 (300~600 μm) | 65.1 | 29.2 | 37.7 | 39.7 | 65.0 | 65.0 | 65.1 |
| | #50~100 (300~150 μm) | 16.2 | 1.5 | 9.4 | 9.4 | 12.8 | 12.6 | 14.5 |
| | More than #100 (less than 150 μm) | 1.1 | 0 | 0.5 | 0.3 | 0.5 | 0.4 | 0.2 |

Referring to Table 1, it is predicted that Comparative Example 1 in which the hydration step was not performed has a low water content and thus, physical crushing will occur during the subsequent transfer process. In addition, it is predicted that Comparative Examples 2 to 4 are controlled to an appropriate water content by the hydration step to suppress crushing during transport, but it was confirmed that due to the non-use of additives or the use of other additives such as polycarboxylic acid or polyethylene glycol during the hydration step, numerous giant particles are produced, thereby exhibiting a decrease in physical properties and a deterioration of productivity of the super absorbent polymer.

In contrast, it was confirmed that in Examples 1 to 3, crushing during transfer could be suppressed by appropriately controlling the water content, but the amount of giant particles produced in the hydration step was also significantly reduced.

The invention claimed is:

1. A method for preparing a super absorbent polymer comprising:
    providing super absorbent polymer particles comprising a base polymer powder including a cross-linked polymer of a water-soluble ethylenically unsaturated monomer having an acidic group of which at least a part is neutralized, and a surface cross-linked layer in which the cross-linked polymer is further cross-linked and which is formed on the base polymer powder,
    mixing the super absorbent polymer particles with water and an additive including a carboxylic acid compound which is a carboxylic acid of an aliphatic hydrocarbon having 10 to 30 carbon atoms to form a hydrated super absorbent polymer.

2. The method for preparing a super absorbent polymer according to claim 1, wherein the carboxylic acid compound is a carboxylic acid is bonded to an end of a linear alkyl group having 12 to 20 carbon atoms.

3. The method for preparing a super absorbent polymer according to claim 1, wherein the carboxylic acid compound is one or more selected from the group consisting of stearic acid, lauric acid, and arachidic acid.

4. The method for preparing a super absorbent polymer according to claim 1, wherein the additive is mixed in an amount of 5 to 20,000 ppmw based on a weight of the super absorbent polymer particles.

5. The method for preparing a super absorbent polymer according to claim 1, wherein the water is mixed in an amount of 1 to 10 parts by weight based on 100 parts by weight of the super absorbent polymer particles.

6. The method for preparing a super absorbent polymer according to claim 1, wherein the mixing of the additive and the water is performed under a temperature of 40 to 80° C.

7. The method for preparing a super absorbent polymer according to claim 1, further comprising drying and classifying the hydrated super absorbent polymer after the mixing of the additive and the water, to form a dried and classified superabsorbent resin that has a particle size of 150 to 850 μm and a water content of 1 to 2.5% by weight.

8. The method for preparing a super absorbent polymer according to claim 7, wherein particles having a particle size of more than 850 μm are removed and form less than 5% by weight based on a total weight of the dried super absorbent resin.

9. The method for preparing a super absorbent polymer according to claim 7, wherein the dried and classified superabsorbent resin has a centrifuge retention capacity (CRC) for a physiological saline solution (0.9 wt. % aqueous sodium chloride solution) for 30 minutes, of 30 to 45 g/g.

10. The method for preparing a super absorbent polymer according to claim 7, further comprising transferring the dried and classified superabsorbent resin.

* * * * *